(12) United States Patent
Cohen-Solal et al.

(10) Patent No.: US 9,317,580 B2
(45) Date of Patent: Apr. 19, 2016

(54) IMAGING PROTOCOL UPDATE AND/OR RECOMMENDER

(75) Inventors: Eric Cohen-Solal, Ossining, NY (US);
Michael Chun-Chieh Lee, Arlington, MA (US); Julien Senegas, Hamburg (DE); Sebastian Peter Michael Dries, Hamburg (DE); Jens Von Berg, Hamburg (DE); Stefanie Remmele, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 248 days.

(21) Appl. No.: 13/983,070

(22) PCT Filed: Jan. 31, 2012

(86) PCT No.: PCT/IB2012/050446
§ 371 (c)(1),
(2), (4) Date: Aug. 1, 2013

(87) PCT Pub. No.: WO2012/104786
PCT Pub. Date: Aug. 9, 2012

(65) Prior Publication Data
US 2013/0311472 A1 Nov. 21, 2013

Related U.S. Application Data

(60) Provisional application No. 61/439,476, filed on Feb. 4, 2011.

(51) Int. Cl.
*G06F 17/30* (2006.01)
*G06F 19/00* (2011.01)

(52) U.S. Cl.
CPC ........ *G06F 17/30598* (2013.01); *G06F 19/321* (2013.01); *G06F 19/325* (2013.01); *G06F 19/3443* (2013.01)

(58) Field of Classification Search
CPC ............ G06F 17/30598; G06F 19/321; G06F 19/325; G06F 19/3443
USPC .......................................................... 707/737
See application file for complete search history.

(56) References Cited

U.S. PATENT DOCUMENTS

2003/0212707 A1   11/2003   Uber et al.
2004/0102958 A1*   5/2004   Anderson, IV ................... 704/4

(Continued)

FOREIGN PATENT DOCUMENTS

DE   102008002882 A1   1/2009
EP      1354554 A2    10/2003

(Continued)

OTHER PUBLICATIONS

Montani, S. et al. "Intelligent Knowledge Retrieval for Decision Support in Medical Applications." Medinfo 2001. Amsterdam. Chapter 6, pp. 498-502.
Kahn, C. et al. "Preliminary Investigation Case-Based Reasoning and Imaging Procedure Selection." IInvestigative Radiology, vol. 29, No. 6, 643-647, 1994.

(Continued)

*Primary Examiner* — Jensen Hu

(57) ABSTRACT

A method includes obtaining electronically formatted information about previously performed imaging procedures, classifying the information into groups of protocols based on initially selected protocols for the previously performed imaging procedures and generating data indicative thereof, identifying deviations between the classified information and the corresponding initially selected protocols for the previously performed imaging procedures, and generating a signal indicative of the deviations. A method includes recommending at least one of a plurality of protocols for an imaging procedure based on at least one of a score, a probability, or a pre-determined rule, which is based on extracted medical concepts from patient information and extracted medical concepts from previously imaged patient information, and generating a signal indicative of the recommendation.

13 Claims, 7 Drawing Sheets

(56) References Cited

U.S. PATENT DOCUMENTS

| | | | |
|---|---|---|---|
| 2005/0234955 A1* | 10/2005 | Zeng et al. | 707/101 |
| 2008/0114564 A1* | 5/2008 | Ihara | 702/158 |
| 2008/0172249 A1* | 7/2008 | Glaser-Seidnitzer et al. | 705/2 |
| 2009/0103794 A1* | 4/2009 | Sathyanarayana | 382/131 |
| 2009/0299926 A1* | 12/2009 | Garrity et al. | 706/14 |
| 2010/0208959 A1* | 8/2010 | Ax et al. | 382/128 |
| 2011/0112856 A1* | 5/2011 | Rousso et al. | 705/2 |
| 2011/0286650 A1* | 11/2011 | Roy et al. | 382/131 |
| 2012/0076386 A1* | 3/2012 | Virmani et al. | 382/131 |
| 2013/0072781 A1* | 3/2013 | Omernick | G06F 19/321 600/410 |

FOREIGN PATENT DOCUMENTS

| | | |
|---|---|---|
| JP | 08131405 | 5/1996 |
| WO | 2004057515 A2 | 12/2003 |

OTHER PUBLICATIONS

Kahn, C. et al. "Appropriateness of Imaging Procedure Requests: Do Radiologists Agree?". AJR: 169, Jul. 1997, pp. 11-14.

Ezzelle, J. et al. "Guidelines on Good Clinical Laboratory Practice: Bridging Operations between Research and Clinical Research Laboratories". National Institutes on Health. J Pharm Biomed Anal. Jan. 7, 2008; 46(1): 18-29.

Kleinpeter, Myra A. "Standardizing Ambulatory Care Procedures in a Public Hospital System to Improve Patient Safety". Advances in Patient Safety: vol. 4, pp. 151-162.

Silver, G. et al. "Standard Operating Procedures for the Clinical management of Patients Enrolled in a Prospective Study of Inflammation and the Host Response to Thermal Injury". American Burn Association, Journal of burn Care & Research, vol. 28, No. 2, pp. 222-230.

* cited by examiner

IMAGING PROTOCOL UPDATE AND/OR RECOMMENDER

This application is a national stage application under 35 U.S.C. §371 of International Application No. PCT/IB2012/050446 filed on Jan. 31, 2012 and published in the English language on Aug. 9, 2012 as International Publication No. WO/2012/104786, which claims priority to U.S. Application No. 61/439,476 filed on Feb. 4, 2011, the entire disclosures of which are incorporated herein by reference.

FIELD OF THE INVENTION

The following generally relates to medical informatics and is described with particular application to updating and/or recommending medical imaging protocols; however, the following is also amenable to other medical and non-medical imaging applications, including, but not limited to, surgery, cardiology, etc. and/or non-medical applications.

BACKGROUND OF THE INVENTION

Radiology departments perform imaging procedures every day. Each of these procedures requires a set of precise specifications of their use. Such precise specifications of use are a protocol. In some cases, especially in larger institutions, the radiologists take the time to formalize their way of working in documents describing their protocols. The edition of such a document is usually done by a group of expert radiologists, after peer-review, using standard, non-dedicated office applications such as a text processing program. The purpose of having written protocols is to ensure consistency, such as for example, by making sure that patients with similar indications are examined the same way and to minimize errors in patient handling and protocol choice and adaptation. Protocols are also useful to train new radiologists and technologists.

Protocols contain different pieces of information that completely define the imaging procedures and serve as guidelines for imaging practices. Examples of such information include a unique name, a modality used (e.g., Computed Tomography (CT), Magnetic Resonance (MR), Nuclear Medicine (NM), X-rays (XR), Ultrasound (US), etc.), body area scanned (e.g., head, chest, etc.), list of clinical indications justifying the use of this specific protocol, list of types of imaging sequences and associated set of parameters, additional comments (e.g., describing the fact that this imaging procedure is a fast acquisition procedure to be used for uncooperative adults or non-sedated children), and patient handling (e.g., preparation, positioning in the scanner, administration of contrast agent, etc.).

Protocols are usually developed for an individual institution having unique practices and local settings: types of modality, types of scanner and types of procedure performed i.e. a trauma center does not perform the same procedures as a cancer center. In particular, for larger institutions (e.g. network of hospitals covering a large population area), multiple radiology departments exist and over the years, develop their own protocols, even if they interact frequently. As practice evolves over time, regular updates of these protocols are necessary to maintain efficiency, diagnostic accuracy and quality of care. The protocols should be consistent throughout a given medical institution.

Such updates are usually done through a committee of expert-radiologists and possibly consultation with specialty doctors with an attempt to incorporate the latest knowledge or newer local practices and achieve a consensus within the radiology department(s). Unfortunately, editing and maintaining up-to-date protocols in a formalized way is a time-consuming activity, which requires high cooperation between the radiologists and technologists of an institution. As a consequence, in many radiology departments, there is no document or system describing the protocols. As such, the expertise and training of the radiologists and technologists is relied upon to assure a certain level of standardization.

An example of how a particular protocol is selected for a particular patient is described next in connection with typical workflow for a patient who is to be imaged. A prescribed order from a referring physician for an imaging examination is received by a radiology department, imaging center or the like. The order typically describes the general type of examination (CT, MRI, PET, US, etc.) and the anatomy to be scanned. Additionally, the order will include the clinical indications that resulted in the order. The clinical indications usually include signs, symptoms, and clinical history, and may also include hypotheses of the underlying disease or condition or mention "rule-out," which also suggests potential conditions that should be investigated in particular.

A radiologist reviews the order and assigns a clinical imaging protocol for the patient based on the specific clinical indications. Other information may also be reviewed to help make this decision, including laboratory data, prior radiology reports, and/or other clinical reports. The clinical imaging protocol defines the settings used on the imaging equipment to acquire the images, and directs the imaging technologist who operates the scanner in how to perform the examination. The protocol as described here will result in an imaging study that is comprised of one or more image series of different geometry or contrast, which in turn are comprised of one or more images. The selection of the protocol generally occurs before the patient is scanned, depending on departmental workflow maybe also hours to days before the patient arrives for the examination.

By way of further example, a patient's imaging order may include the indication "hearing loss in left ear," with the note to perform an "MRI of the head." Within this general examination type, there are many options of clinical imaging protocols that are used specifically by the imaging centre or radiology department. Examples that are under the general category "MRI of the head" may include "brain tumor," "multiple sclerosis," "angiography," "MR without contrast," "internal auditory canal," "eye-orbit," to name a few. A radiologist reading this order may decide that the order is best fulfilled by using the "internal auditory canal" protocol.

Conventional software applications that facilitate a radiologist with selecting a protocol generally are focused on digitizing what has previously been a paper process. Such applications electronically collect the order and other clinical information about the patient, and provide a digital list of clinical scan protocols for a radiologist to manually choose from. Unfortunately, such solutions do not provide assistance in choosing a particular one of the listed protocols. As a result, protocol selection consumes radiologist time and is susceptible to human error, and there tend to be inconsistencies between selected protocols amongst radiologists, even in the same imaging facility.

SUMMARY OF THE INVENTION

Aspects of the present application address the above-referenced matters, and others.

According to one aspect, a method includes obtaining electronically formatted information about previously performed imaging procedures, classifying the information into groups of protocols based on initially selected protocols for the previously performed imaging procedures and generating data indicative thereof, identifying deviations between the classified information and the corresponding initially selected protocols for the previously performed imaging procedures, and generating a signal indicative of the deviations.

According to another aspect, a method includes obtaining electronically formatted information about previously performed imaging procedures, clustering the imaging procedures into clusters based on a similarity of imaging parameters from the obtained information and generating data indicative thereof, and generate a signal indicative of one or more candidate protocols based on the data.

According to another aspect, a system includes a storage medium that stores computer readable instructions for at least one of updating an existing imaging protocol or creating a new imaging protocol and one or more processors, which execute the computer readable instructions. The stored computer readable instructions, when executed by the one or more processors, cause the one or more processor to obtain at least clinical indications for previously performed imaging procedures, types of the previously performed imaging procedures, and parameters used for the previously performed imaging procedures, and at least one of generate an update recommendation for a protocol corresponding to one of the previously performed imaging protocols based on the obtained information or generate one or more candidate new imaging protocols based on the obtained information.

According to one aspect, a method includes obtaining electronically formatted patient information for a patient scheduled for an imaging procedure via an imaging system, wherein the patient information includes at least clinical indications for the patient, and extracting medical concepts from the patient information, obtaining electronically formatted previously imaged patient information for one or more previously imaged patients, and extracting medical concepts from the previously imaged patient information, obtaining electronically formatted existing imaging protocols, and recommending at least one of the protocols for the imaging procedure based on at least one of a score, a probability, or a pre-determined rule, which is based on the extracted medical concepts from the patient information and the extracted medical concepts from the previously imaged patient information, and generating a signal indicative of the recommendation.

According to another aspect, a computing system includes computer readable storage medium encoded with instructions for determining one or more candidate relevant additional concepts and one or more processors configured to execute the instructions. The one or more processors, when executing the instructions, extracts medical concepts from patient information for a patient scheduled for an imaging procedure via an imaging system, extracts medical concepts for previously imaged patients, and recommends at least one protocol for the imaging procedure based on at least one of a score, a probability, or a pre-determined rule, which is based on the extracted medical concepts from the patient information and the extracted medical concepts for the previously imaged patient information. A display is configured for presenting the recommended at least one protocol for the imaging procedure.

According to another aspect, a computing readable storage medium is encoded with computer readable instructions, which, when executed by one or more processor of a computing system, cause the computer system to identify and recommend at least one of the protocols for an imaging procedure for a patient based on at least one of a score, a probability, or a pre-determined rule, which is based on extracted medical concepts from patient information for the patient and extracted medical concepts from patient information for previously imaged patients

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
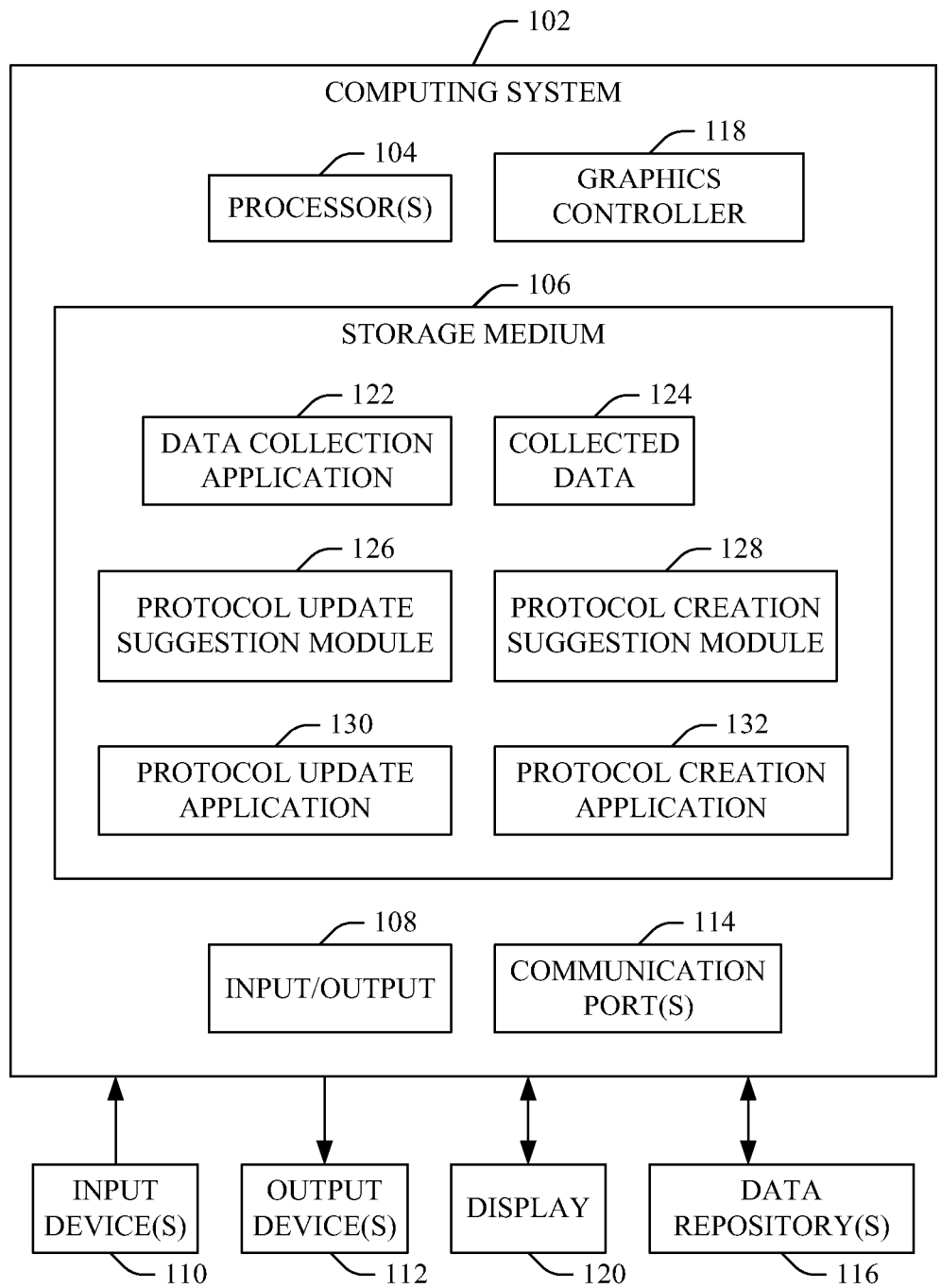
FIG. 1 illustrates an example system that includes a processor(s) and storage with computer readable instructions for updating protocols.

FIG. 1 illustrates an example computing system 102 such as a workstation, a computer, or the like. The computing system 102 includes one or more processors 104 and computer readable storage medium 106 (e.g., physical memory) encoded or embedded with computer readable instructions, which, when executed by the one or more processors 104 cause the system 102 to carry out various functions.

Although the storage medium 106 is shown as a single component, it is understood that the storage medium 106 may include a plurality of storage units, including storage local to the computing system 102 and/or storage external from the computing system 102. Additionally or alternatively, the one or more processors 104 execute instructions carried by transitory medium such as a signal carrier.

Input/output 108 is configured for receiving information from one or more input devices 110 (e.g., a keyboard, a mouse, and the like) and conveying information to one or more output devices 112 (e.g., a printer, a CD writer, a DVD writer, portable flash memory, etc.).

One or more communications ports 114 are configured for communication with an intranet (e.g., within a facility department), an internet (e.g., within and/or amongst facilities), and/or the Internet through various connectors, cables, interfaces, etc. In the illustrated embodiment, the one or more communications ports 114 are configured for communication with one or more data repositories 116.

In the context of a radiology use case scenario, the one or more data repositories 116 may include one or more of a picture archiving and communication system (PACS), a radiology information system (RIS), a hospital information system (HIS), an electronic medial record (EMR), a database, a server, an imaging system, a computer and/or other data repository. Such data may be stored in standard formats such as Digital Imaging and Communications in Medicine (DICOM) and/or other standard formats, and/or non-standard, proprietary, and/or other format. A graphics controller 118 processes data for presentation on a monitor such as display 120 in a human readable format.

The storage medium 106 stores various software applications, software modules, and data, which are discussed next, for updating protocols.

As shown, in the illustrated embodiment, the storage medium 106 includes a data collection application 122 that communicates with various data repositories of the one or more data repositories 116 and/or other data repository(s) and retrieves electronically formatted information therefrom. With continuing reference to the radiology use case scenario, the data collection application 122 collects information about prior imaging examinations performed on patients. This information includes, but is not limited to, clinical indications, imaging procedures (e.g., head scan, liver scan, etc.), the set of parameters used for each imaging procedure, and/or other available information about prior imaging procedures. In the illustrated embodiment, the retrieved information is stored as collected data 124 in the storage medium 106 and/or in other local storage and/or storage remote from the computing system 102.

A protocol update suggestion module 126 evaluates the collected data 124 and provides information that can be utilized to update existing protocols based on the collected data 124. As described in greater detail below, in one instance, the protocol update recommendation module 126 compares data from the collected data 124 corresponding to how a particular protocol has been executed with the corresponding protocol, and generates and provides information, based on the comparison, that can be utilized to update the protocol. The information can be presented via the display 120, stored, or conveyed to a component external to the computing system 102, etc.

A protocol creation suggestion module 128 evaluates the collected data 124 and provides information that can be utilized to create a new protocol based on the collected data 124. As described in greater detail below, in one instance, the protocol creation suggestion module 128 employs a data mining technique to extract clinical indications, corresponding imaging procedures, and associated parameters, and to group together similar practices, which can be utilized to facilitate a user with determining whether to create a new protocol. The information can be presented via the display 120, stored, or conveyed to a component external to the computing system 102, etc.

In a variation of the illustrated embodiment, either of the protocol update module 126 or protocol creation module 128 can be omitted A protocol update application 130 provides a user interface and software tools through which a user can view the information provided by the protocol update suggestion module 126 and/or interact with the module 126 to modify an existing protocol.

A protocol creation application 132 provides a user interface and software tools through which a user can view the information provided by the protocol creation suggestion module 128 and/or interact with the module 128 to create a new protocol. The protocol creation application 132 may also be utilized when the user determines to create a new protocol rather than update an existing protocol.

The information from the modules 126 and 128 can be presented individually and/or in combination, with or without other information. Examples of other information include, but are not limited to, an imaging capability of a new or existing imaging system that has not been taken into account already, a change to a guideline used to generate a protocol, a protocol rule from a source outside of an imaging facility, etc. Individually, as discussed above, a protocol recommendation can be used to update an existing protocol, split a protocol into multiple protocols, and/or create a new protocol. In combinations, the information can be used to develop a new set of protocols taking into account both the expert-radiologists views and the more recent practices that might reveal novel and better diagnostic imaging procedures. The result also gives the ability to re-examine the current protocols and complement them with new ones reflected in the daily practice of imaging examinations.

In either instance, the recommendation, existing protocols, and/or other information can be concurrently displayed so that a clinician can view, compare, and use the information to update existing protocols and/or create new protocols, and/or confirm updated and/or newly created protocols. The presented recommendations can be variously highlighted (via color, size, outlining, etc.) and/or sorted (e.g., based on tissue of interest, etc.) in order of appropriateness to the patient. Updates can be executed through interaction between a clinician and the protocol update application 130 and/or the protocol creation application 132 in which the recommendations are displayed as user selectable options (e.g., graphical icons, menu options, etc.) and are selected by the users via touchscreen technology, a mouse or the like, a digital pen, a voice command (via voice recognition software), a keyboard, etc. The update and/or new protocols can be stored on one or more particular imaging systems, in one or more of the data repositories 116, and/or elsewhere and utilized for performing imaging examinations. Updated and/or new protocols in the repositories 116 can be collected as described above when subsequently updating and/or generating protocols.

In the illustrated embodiment, the data collection application 122, the collected data 124, the protocol update suggestion module 126, the protocol creation suggestion module 128, the protocol update application 130, and the protocol creation application 132 are shown in the storage medium 106. However, it is to be appreciated that one or more of the data collection application 122, the collected data 124, the protocol update suggestion module 126, the protocol creation suggestion module 128, the protocol update application 130, and the protocol creation application 132 can be located in other local storage medium and/or external storage medium, including on a single storage medium or distributed across multiple storage mediums.

Figure 2:
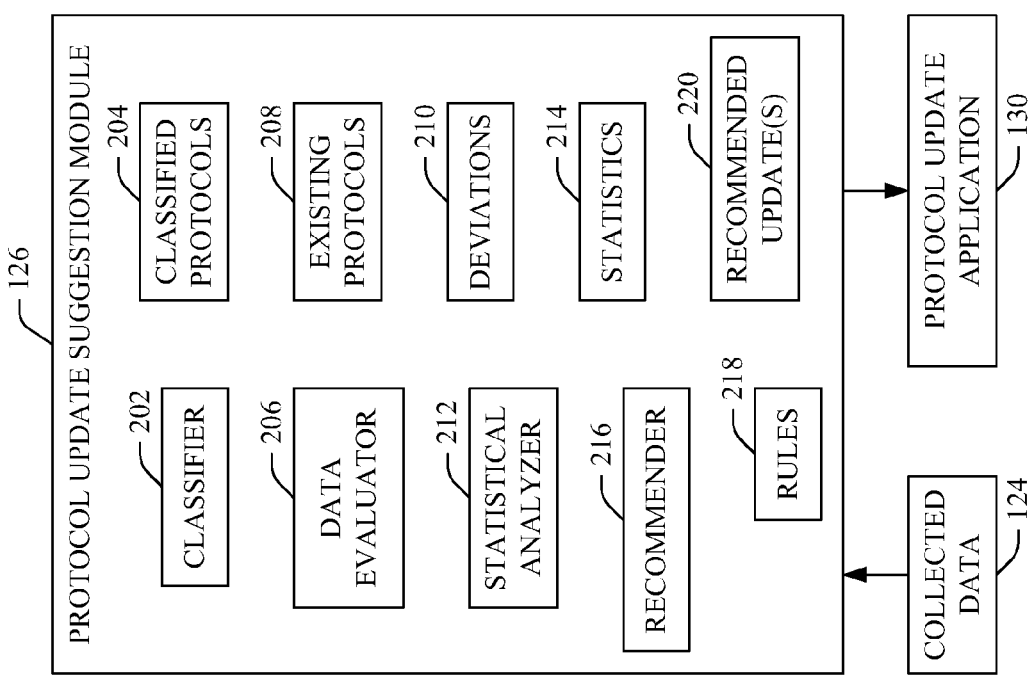
FIG. 2 illustrates an example protocol update suggestion module.

As briefly discussed above, the protocol update suggestion module 126 evaluates the collected data 124 and provides information that can be utilized to update existing protocols based on the collected data 124. FIG. 2 illustrates a non-limiting example of the protocol update suggestion module 126.

A classifier 202 classifies the collected data 124. In the illustrated embodiment, the classifier 202 classifies each procedure in the collected data 124 based on the corresponding initially selected protocols. By way of example, if a head protocol is initially selected for a procedure, the protocol is classified as a head protocol regardless of any deviation from the initial protocol. The initial protocol type or name can be retrieved from a name of the initially selected protocol, a file header, metadata, and/or otherwise. Where the initially selected protocol is modified, the modified protocol generally will include information linking the modified protocol to the initially selected protocol. In the illustrated embodiment, the classified collected data is stored as classified protocols 204.

A data evaluator 206 evaluates the classified protocols 204 based on existing protocols 208, which were either developed manually by a group of expert-radiologists or assisted by the use of the protocol update suggestion module 126. In the illustrated embodiment, for each set of prior imaging examinations belonging to the same protocol, the data evaluator 206 compares the sets with the corresponding protocol and determines any deviations there between. The data evaluator 206 generates a signal indicative of any deviations, which, in the illustrated embodiment, is stored as deviations 210. Examples of such deviations are provided next.

In one instance, the deviations may include clinical indication(s) different from the ones specified in the initial protocol. This may indicate a possible extension in the way a protocol is used or a misuse of it. The deviations may be obtained by extracting clinical terms from the free text clinical indications stored in the information collection subsystem using known techniques such as natural language processing (NLP), etc. Additionally or alternatively, the deviations may include parameter changes. For example, at the moment of acquisition, depending on the specifics regarding a patient, the technologist might decide to change some of the parameters. In this instance, the deviations may indicate a range, mean, median, standard deviation, and/or quartiles of parameters actually used in the collected data 124.

Additionally or alternatively, the deviations may include information indicative of imaging procedures specified in a protocol that were not performed (e.g., because they were not deemed necessary) and/or additional imaging procedures, which were not specified in the protocol, that were performed. An example of the former case is when the selected protocol corresponds to an extended version of the required examination and contains by default imaging procedures that are only done optionally in practice. An example of the latter case is when additional findings are observed while images are being acquired. In some of those cases, a radiologist may then select one or more additional imaging procedures to perform.

A statistical analyzer 212 processes the deviations 210 and generates a signal indicative of statistics of the different deviations (e.g., frequency of the deviations). The statistics can reveal a new range of use for particular parameters like an expanded or a shifted range. Another example could show how often an additional imaging procedure is used and with which clinical indication(s). In the illustrated embodiment, the signal is stored as statistics 214.

A recommender 216 generates a signal indicative of recommended updates for a protocol based on the deviations 210 and/or statistics 214. As such, the recommended updates may reflect current trends and/or more recent practices. The recommendation may be in the form of a candidate updated protocol that can be accepted, modified and/or rejected, or suggestions that can be added to a protocol via a user editing a protocol. In the illustrated embodiment, signal is stored as recommended update(s) 220. Optional rules 218 may be employed by the recommender 216 for making recommendations. As an example, one rule may indicate that if a parameter value has been set to a new value outside the usual range of value for more than 50% of the cases, the recommender 216 recommends updating the protocol to expand the range of values to include the newly used value.

Where an existing protocol alone can not any longer represent a self-contained description of a particular imaging procedure, the recommendation may indicate that the existing protocol should be divided into multiple protocols, which may be achieved by splitting the protocol into multiple protocols and/or creating a new protocol. Example of where this might happen is when prior practices show that the protocol use has expanded beyond its original intent and that splitting the protocol may better describe current clinical practices. The rules 218 can be employed to facilitate making such a recommendation.

The deviations 210, the statistics 214, and/or the recommended update(s) 220 are conveyed to the protocol update application 130, which is used to facilitate updating existing protocols. The deviations may additionally or alternatively be used to provide a picture of the current practices and the possibility to review the rationale for deviations from the protocols, determine a quality-compliance metric, identify best practices, etc.

Although the components 202-220 are shown as part of the protocol update suggestion module 126, it is to be appreciated that one or more of the components 202-220 can be part of other modules, including a single module or distributed across multiple modules.

Figure 3:
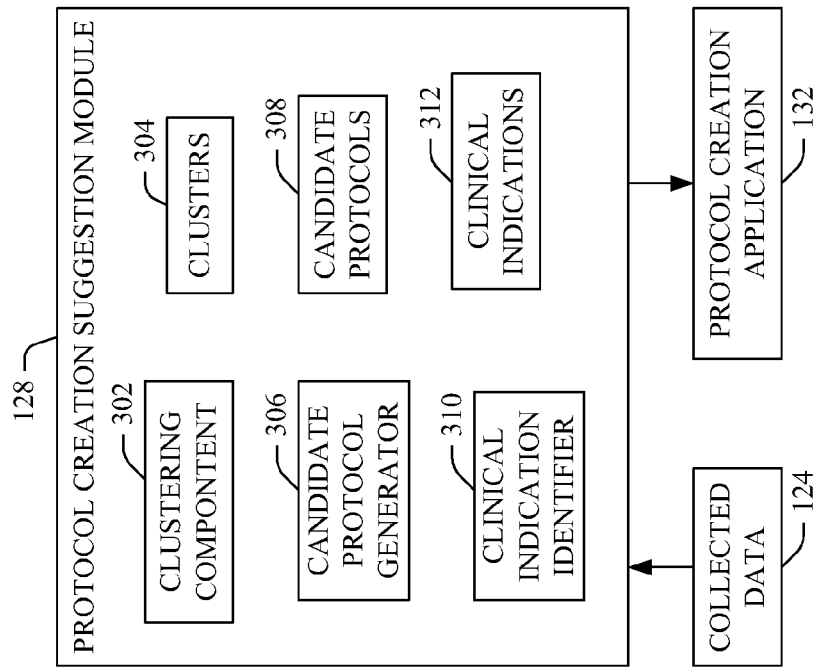
FIG. 3 illustrates an example protocol creation module.

As briefly discussed above, the protocol creation suggestion module 128 evaluates the collected data 124 and provides information that can be utilized to create new protocols based on the collected data 124. FIG. 3 illustrates a non-limiting example of the protocol creation suggestion module 128

A clustering component 302 clusters imaging procedures in the collected data 124 into multiple clusters 304 based on the utilized scan parameters, such as all parameters or a sub-set of the most relevant parameters, which may be preselected and which represent a feature space of interest. Generally, each point in cluster space represents one performed image procedure, and the resulting clusters are groups of similar imaging parameters. Thus, imaging procedures for which the parameters are identical or for which the parameters have changed only slightly are grouped together. Various cluster algorithms can be employed, such as, but not limited to, k-means, c-means, self-organizing maps, hierarchical clustering, etc. clustering algorithms.

A candidate protocol generator 306 generates one or more candidate protocols 308 based on the clusters 304 by grouping similar imaging procedures together. Each candidate protocol contains a plurality of imaging procedures, and imaging procedures belong to the same group when they mostly contain the same set of imaging parameters. The candidate protocols 308 might be, at this point, very close to the existing protocols if the imaging practices remain very close to the protocol description. Otherwise, the candidate protocols 308 will show new trends in the way imaging procedures are performed and could produce procedure types, which can be fairly different from the existing protocols.

A clinical indication identifier 310 identifies clinical indications associated with each type of protocols from the candidate protocols 308 and builds a list of clinical indications 312 as the aggregation of the identified clinical indications. This list may be organized by concept in order to categorize the list into a more comprehensive, shorter list of groups of clinical indications. Several approaches can be used, individually or in combination to organize the list. For example, in one instance, an ontology-based approach is used to identify synonyms or to group medical concepts which are related through a parent-child relationship or other relationships. Additionally or alternatively, a statistical approach that highlight significant associations between terms and group them as related can be utilized.

In general, significant associations between medical terms could be obtained from different sources to build a database of these known associations. They could be built manually by medical experts or they could be derived from data. In the latter case, the associations could be identified through co-occurrence frequencies between medical concept terms in a collection of reports, or scholarly articles (e.g. medical journals), clinical textbooks on specific domains. To extract then the most significant ones, statistical techniques could be applied like the Fisher's exact test or Chi-square tests.

The candidate protocols 308 and/or the list of clinical indications 312 are conveyed to the protocol creation application 132 to facilitate creating new protocols. For example, the candidate protocols and/or the list of clinical indications can be displayed, for example, as a hierarchical representation using example body part and sub-anatomical regions to structure the list of protocols in a meaningful manner for analysis by expert-radiologists and/or other authorized personnel.

Figure 4:
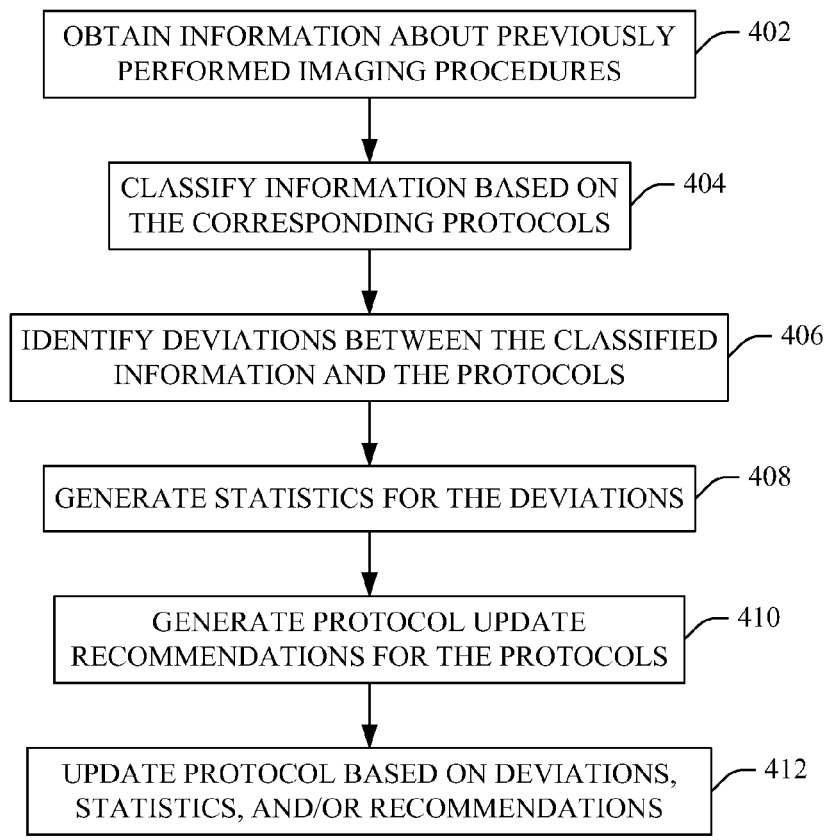
FIG. 4 illustrates an example method for updating protocols.

FIG. 4 illustrates method for updating a protocol. It is to be appreciated that the ordering of the acts in the methods described herein is not limiting. As such, other orderings are contemplated herein. In addition, one or more acts may be omitted and/or one or more additional acts may be included.

At 402, electronically formatted information about previously performed imaging procedures is obtained.

At 404, the information is classified based on the corresponding protocols.

At 406, deviations between the classified information and the corresponding protocols are identified.

At 408, statistics for the deviations are generated based on the deviations.

At 410, recommendations for updating the corresponding protocols are generated based on the statistics. As discussed herein, one or more rules can optionally be used to facilitate generating recommendations.

Figure 5:
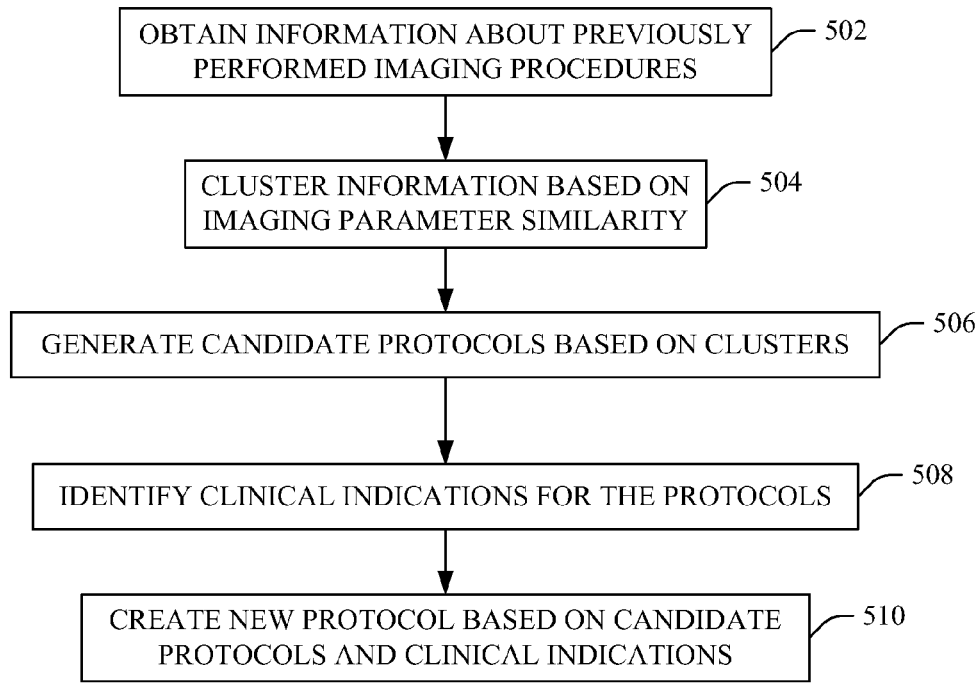
FIG. 5 illustrates an example method for creating protocols.

At 412, at least one of the deviations, the statistics, or the recommendations is presented and utilized to update an existing protocol FIG. 5 illustrates method for creating a new protocol. It is to be appreciated that the ordering of the acts in the methods described herein is not limiting. As such, other orderings are contemplated herein. In addition, one or more acts may be omitted and/or one or more additional acts may be included.

At 502, electronically formatted information about previously performed imaging procedures is obtained.

At 504, the information is clustered based on imaging parameter similarity.

At 506, one or more candidate protocols are generated based on the clusters.

At 508, clinical indications are identified from the candidate protocols.

At 510, the candidate protocols and the clinical indications are utilized to create one or more new protocols.

As discussed in connection with FIG. 1, the methods of FIGS. 4 and 5 can be used in combination to develop a new set of protocols taking into account both the expert-radiologists views and the more recent practices that might reveal novel and better diagnostic imaging procedures, and the result also gives the ability to re-examine the current protocols and complement them with new ones reflected in the daily practice of imaging examinations.

The above may be implemented by way of computer readable instructions, which when executed by a computer processor(s), cause the processor(s) to carry out the described acts.

Figure 6:
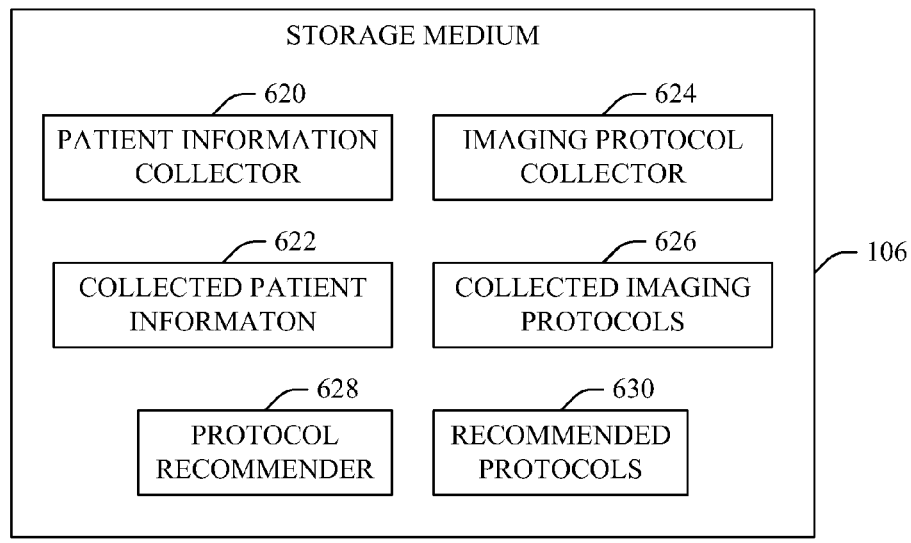
FIG. 6 illustrates an embodiment in which the storage includes computer readable instructions for recommending protocols.

FIG. 6 illustrates an embodiment in which the computer readable storage medium 106 stores various software applications, software modules, and/or data, which are discussed next, for recommending protocols. As shown, in the illustrated embodiment, the storage medium 106 includes at least a patient information collector 620, collected patient information 622, an imaging protocol collector 624, collected imaging protocols 626, a protocol recommender 628, and recommended protocols 630.

The patient information collector 620 communicates with various data repositories of the one or more data repositories 116 and/or other data repository(s) and retrieves electronically formatted information (collected patient information 622) therefrom for a particular subject to be scanned. With continuing reference to the radiology use case scenario, the patient information collector 620 at least collects clinical indications (e.g., signs, symptoms, etc.) of the patient corresponding to the imaging procedure. Other collected information includes, but is not limited to, physician prescribed order information, laboratory information, prior imaging reports, prior non-imaging reports, and/or other information.

The imaging protocol collector 624 also communicates with various data repositories of the one or more data repositories 116 and/or other data repository(s) and retrieves electronically formatted information therefrom. With continuing reference to the radiology use case scenario, the imaging protocol collector 624 at least collects a list of imaging protocols (collected imaging protocols 626)

The protocol recommender 628 recommends protocols for scanning the subject based on the collected patient information 622 and the collected imaging protocols 626. The illustrated protocol recommender 628 is configured to at least, for a given collected protocol, generate a value that represents an appropriateness of the given collected protocol for scanning the patient. This can be done for all of the collected protocols or a sub-set thereof. As described in greater detail below, in one non-limiting instance, the resulting values may represent scores that indicate a degree of appropriateness based on historical patient information, probabilities that indicate a likelihood of appropriateness, appropriateness based on a predetermined set of rules, and/or a combination thereof.

The values can be variously presented and/or utilized, for example, to facilitate a radiologist and/or other authorized personnel with selecting a protocol for the patient to be imaged. Using the recommendation as such may reduce errors and inconsistencies associated with selecting protocols manually and may reduce the amount of time required by a radiologist and/or other authorized personnel to perform this task. Providing such information may improve confidence in decision making and/or have training and/or learning effect for radiologists and/or other personnel.

By way of non-limiting example, the collected patient information 622 and the recommended protocols 630 can be presented via a graphical user interface (GUI) to the user via the display 120. The presentation of the suggested protocol may be communicated to the user by presenting the possible protocols as a sorted list, a filtered list, an unsorted list, graphical representation, etc. The user can then choose to accept and/or modify the suggested protocol or choose a different protocol. Information indicative of acceptance of, modification to and/or rejection of a recommended protocol can be included in the knowledge base underlying the protocol recommender 628, and an accepted protocol can be conveyed to the imaging system used to image the patient.

In the illustrated embodiment, the patient information collector 620, the collected patient information 622, the imaging protocol collector 624, the collected imaging protocols 626, the protocol recommender 628, and the recommended protocols 630 are shown in the storage medium 106. However, it is to be appreciated that one or more of 620-630 can be located in other local storage medium and/or external storage medium, including on a single storage medium or distributed across multiple storage mediums.

Figure 7:
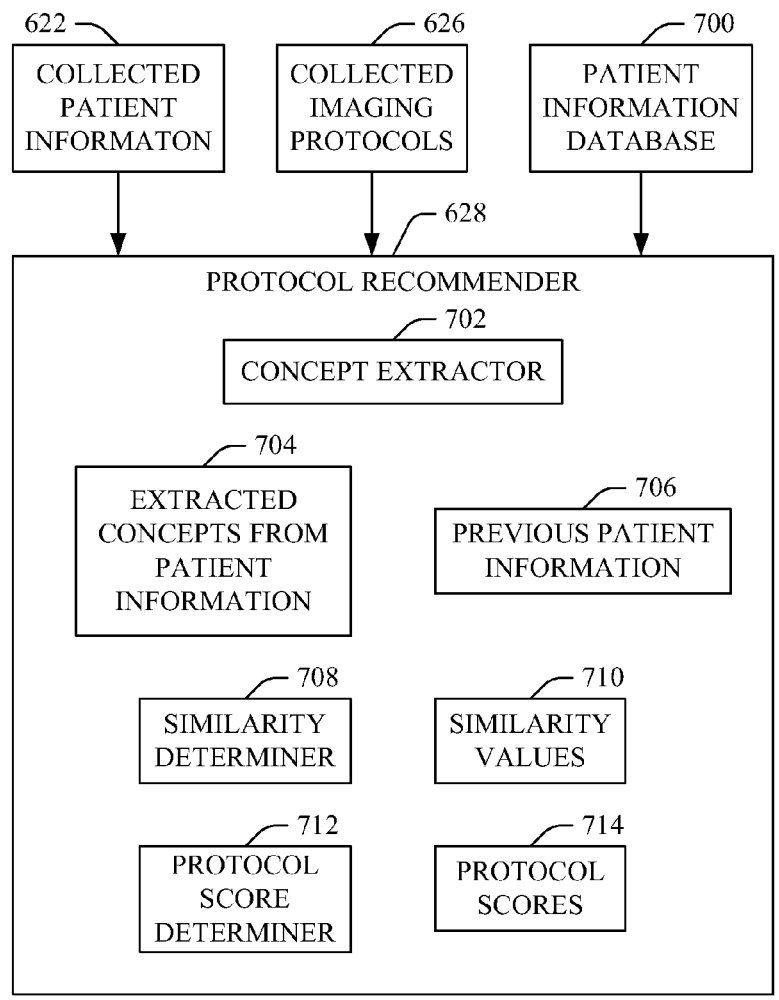
FIG. 7 illustrates an example protocol recommender that recommends protocols based on similarity metrics.
Figure 8:
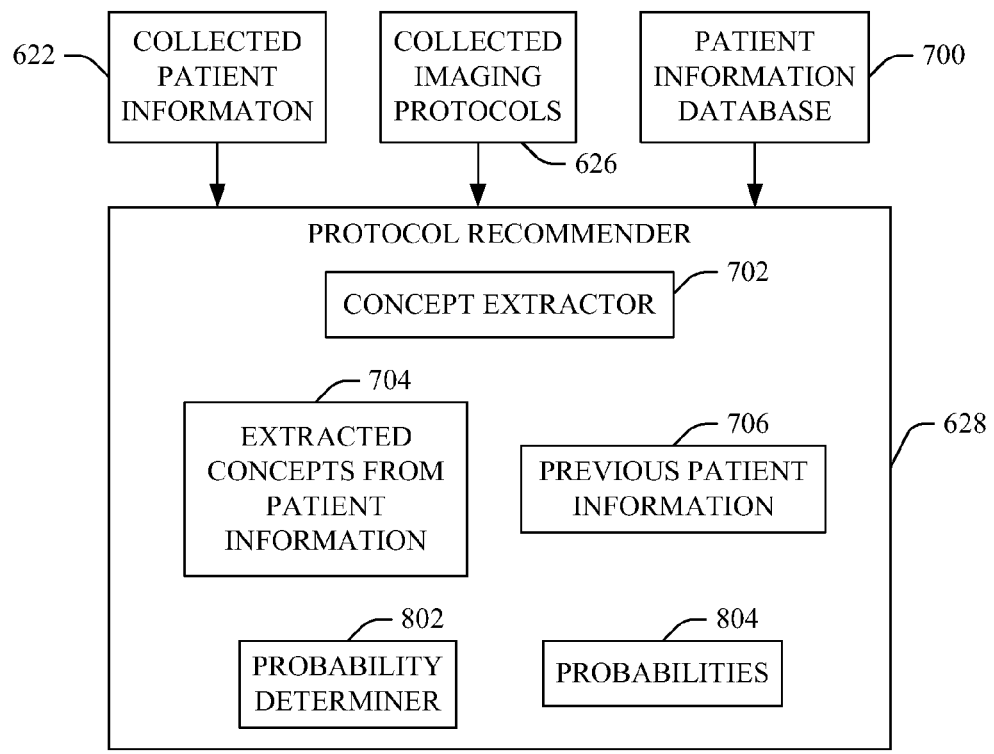
FIG. 8 illustrates an example protocol recommender that recommends protocols based on probabilities.
Figure 9:
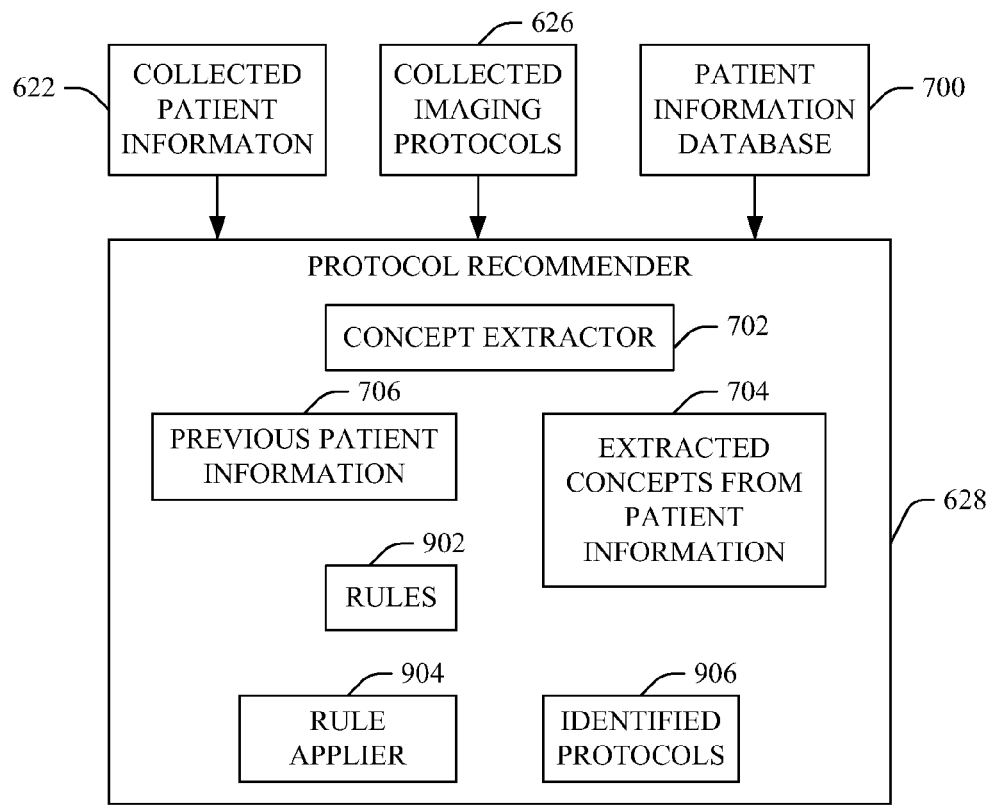
FIG. 9 illustrates an example protocol recommender that recommends protocols based on a set of rules.

FIGS. 7, 8 and 9 illustrate variations of the protocol recommender 628.

FIG. 7 illustrates an example of the protocol recommender 628 configured to generate an output signal indicative values that represent scores that indicate a degree of appropriateness of the protocols for the patient to be scanned based on historical patient information.

A concept extractor 702 extracts medical concepts from the collected patient information 622. Where the information 622 includes free text, the concept extractor 702, optionally, can employ a natural language processing algorithm or the like to extract a list of medical concepts that may be given as strings (e.g. "tinnitus"), coded values (e.g. "UMLS:C0040264"), and/or other text based format. In the illustrated embodiment, the extracted concepts are stored as extracted concepts from patient information 704.

The concept extractor 702 also extracts medical concepts from data for previous patients from a patient information database 700. The extracted medical concepts are stored, along with the imaging protocols that were performed for the previous patients, as previous patient information 706. The patient information collector 620 and/or other component can be used to obtain the source data of the previous patients.

A medical concept similarity determiner 708 determines a similarity between the medical concepts for the patient to be scanned and at least one of the previous patients and generates a signal indicative thereof. The signal includes a similarity value (e.g., a single computed value) for each prior patient, or similarity values 710.

Default and/or user defined weights can be used to weight different medical concepts based on importance and/or otherwise. Various similarity measuring approaches can be used. For example, suitable approaches include, but are not limited to, cosine similarity, Hamming distance, etc. Query expansion and/or other approach to expand the information can optionally be employed by the determiner 708.

A protocol score determiner 712 determines protocol scores 714, or a score for each type of protocol in the collected imaging protocols 626. In one instance, a score 714 is determined by computing a mathematical function of the similarity values for all or a subset of the prior patients for which the protocol was used. In this instance, the final score for a given protocol is computed as an average or weighted average of the similarity values for all previous patients scanned using the given protocol.

The extracted concepts from patient information 704, the previous patient information 706, the similarity values 710, and/or the protocol scores 714 can be presented via the display 120, conveyed to one or more other components, utilized to select a protocol, etc. as described in greater detail below.

FIG. 8 illustrates an example of the protocol recommender 628 configured to generate an output signal indicative of one or more values that represent probabilities that indicate a degree of appropriateness of the protocols for the patient to be scanned.

In this example, the recommender 628 includes that concept extractor 702 (FIG. 7), which, as discussed above, extracts medical concept from the patient to be scanned (the extracted concepts from patient information 704) and data for previous patients (the previous patient information 706).

A probability determiner 802 determines one or more probabilities 804, such as a probability for each protocol given the clinical indications found in the patient to be scanned and generates a signal indicative thereof. In one instance, the probability is a Bayesian probability, which can be expressed as: $P(protocol_A | term_1, term_2, \ldots term_n)$, wherein where the probability for a given protocol is a function of a number of co-occurrences of n terms (n=an integer equal to or greater than one) with the given protocol to the total number of occurrences of the n terms within individual patient information.

The extracted concepts from patient information 704, the previous patient information 706, and/or the probabilities 804 can be presented via the display 120, conveyed to one or more other components, utilized to select a protocol, etc. as described in greater detail below.

FIG. 9 illustrates an example of the protocol recommender 628 configured to generate an output signal indicative values that represent a degree of appropriateness of the protocols for the patient to be scanned based on a predetermined set of rules.

In this example, the recommender 628 includes that concept extractor 702 (FIG. 7), which, as discussed above, extracts medical concept from the patient to be scanned (the extracted concepts from patient information 704) and data for previous patients (the previous patient information 706).

Rules 902 include a mapping between medical concepts in the extracted concepts form patient information 704 and the collected imaging protocols 626. Generally, each protocol may have one or more medical concepts associated with it. For example, the rules 902 may include a mapping indicating protocol 1 is relevant to disease A, condition B, disease C, etc.

A rule applier 904 identifies protocols (identified protocols 906) based on the mapping.

The extracted concepts from patient information 704, the previous patient information 706, the rules 902, and/or the identified protocols 906 can be presented via the display 120, conveyed to one or more other components, utilized to select a protocol, etc. as described in greater detail below.

It is to be appreciated that the examples illustrated in FIGS. 7, 8 and 9 can be employed individually or combination. By way of example, in one instance, the collected patient information 622 is used along with the scores 714 to recommend a protocol. In another instance, the collected patient information 622, the protocol scores 714, the probabilities 804, and the identified protocols 906 are used individually or concurrently to recommend a protocol.

Recommended protocols can be presented, viewed, compared, and used by a clinician for determining a protocol for a patient. The presented information can be variously highlighted (via color, size, outlining, etc.) and/or sorted (e.g., based on tissue of interest, etc.) in order of appropriateness to the patient. The extracted medical concepts about the previously imaged patients, the extracted medical concepts about the patient, and/or other information can be additionally or alternatively displayed and highlighted.

Furthermore, the recommended protocols can be displayed as user selectable options (e.g., graphical icons, menu options, etc.) and can be selected by the users via touchscreen technology, a mouse or the like, a digital pen, a voice command (via voice recognition software, a keyboard, etc. A selected protocol can be conveyed from the computing system 102 to another system such as the imaging scanner that will be to scan the patient via the communication ports 114 and/or otherwise using proprietary and/or standard approaches such as by encoding the protocol as a RIS Procedure ID and transmitting via the DICOM modality worklist. The protocol can be automatically loaded and loaded via user interaction.

FIGS. 10-13 illustrate example method for recommending protocols. It is to be appreciated that the ordering of the acts in the methods described herein is not limiting. As such, other orderings are contemplated herein. In addition, one or more acts may be omitted and/or one or more additional acts may be included.

Figure 10:
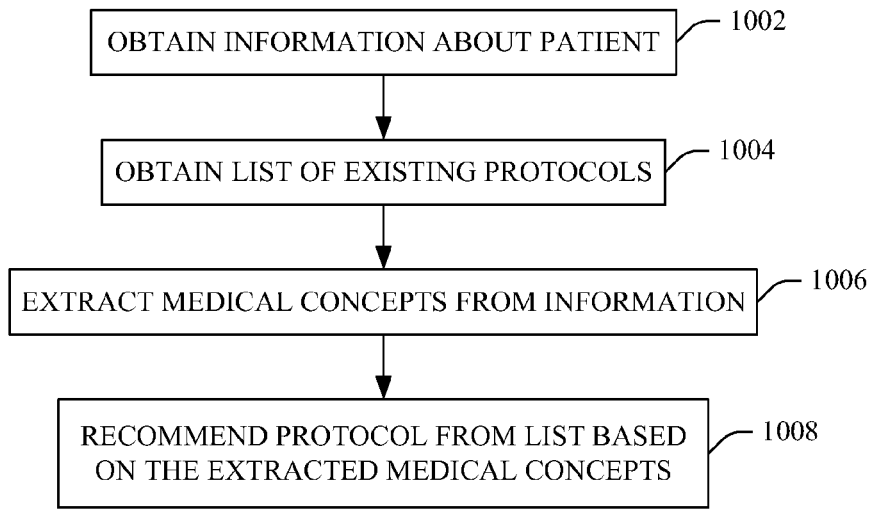
FIG. 10 illustrates example methods for recommending an imaging protocol for a patient to be scanned.

FIG. 10 illustrates an example method for recommending an imaging protocol for a patient to be scanned.

At 1002, information, in electronic format, about a patient to be scanned is obtained. Such information at least includes clinical indications for the patient.

At 1004, a list, in electronic format, of existing imaging protocols is obtained.

At 1006, medical concepts are extracted from the information about the patient to be scanned.

At 1008, an imaging protocol from the list is recommended for the patient based at least on the extracted medical concepts.

Figure 11:
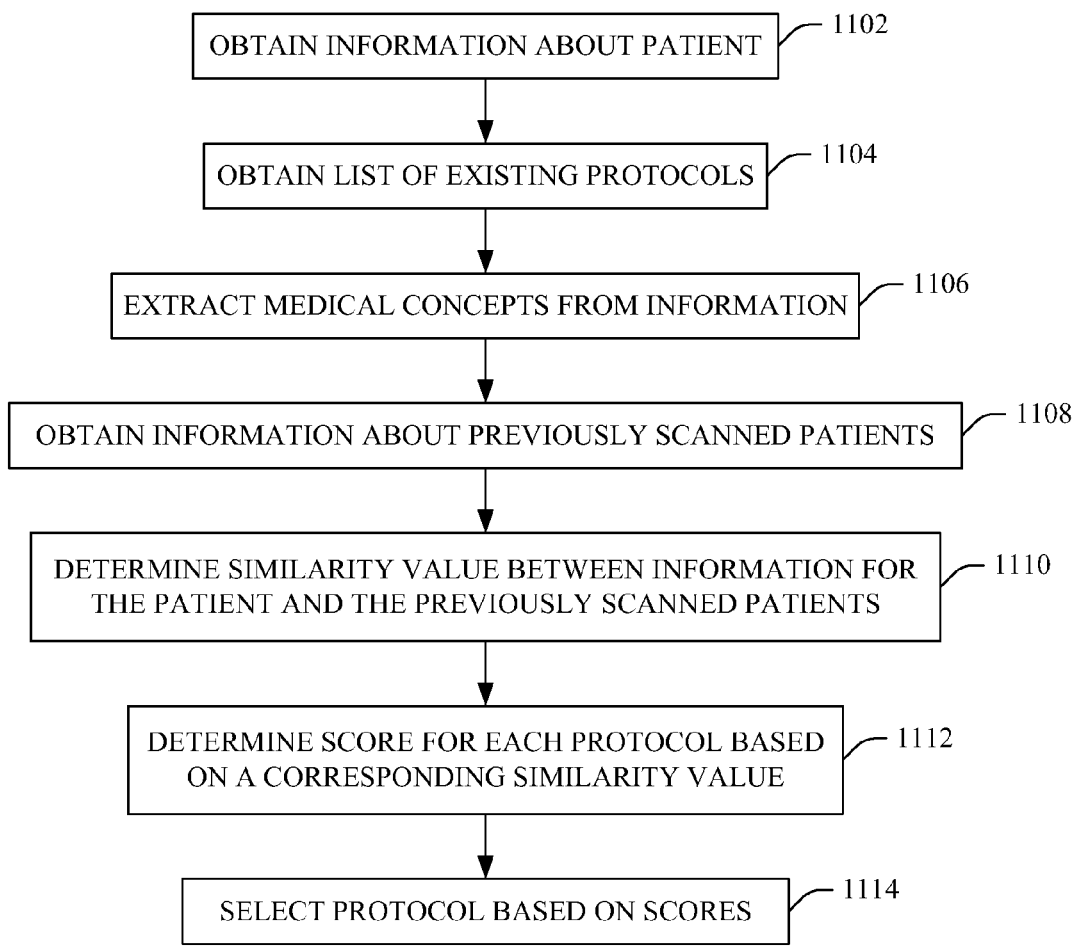
FIG. 11 illustrates an example method for recommending an imaging protocol for a patient to be scanned based on similarity of medical concepts between the patient and previously scanned patients.

FIG. 11 illustrates an example method for recommending an imaging protocol for a patient to be scanned based on similarity of medical concepts between the patient and previously scanned patients.

At 1102, information, in electronic format, about a patient to be scanned is obtained. Such information at least includes clinical indications for the patient.

At 1104, a list, in electronic format, of existing imaging protocols is obtained.

At 1106, medical concepts are extracted from the information about the patient to be scanned.

At 1108, information, in electronic format, about previous patients is obtained. Such information includes at least extracted clinical indications and previous protocols used for scanning the previous patients.

At 1110, similarly values between the medical concepts of the patient to be scanned and the previously scanned patients are determined.

At 1112, a score for each protocol based on the similarity values is determined as described herein.

At 1114, a protocol is selected for the patient based on the scores.

Figure 12:
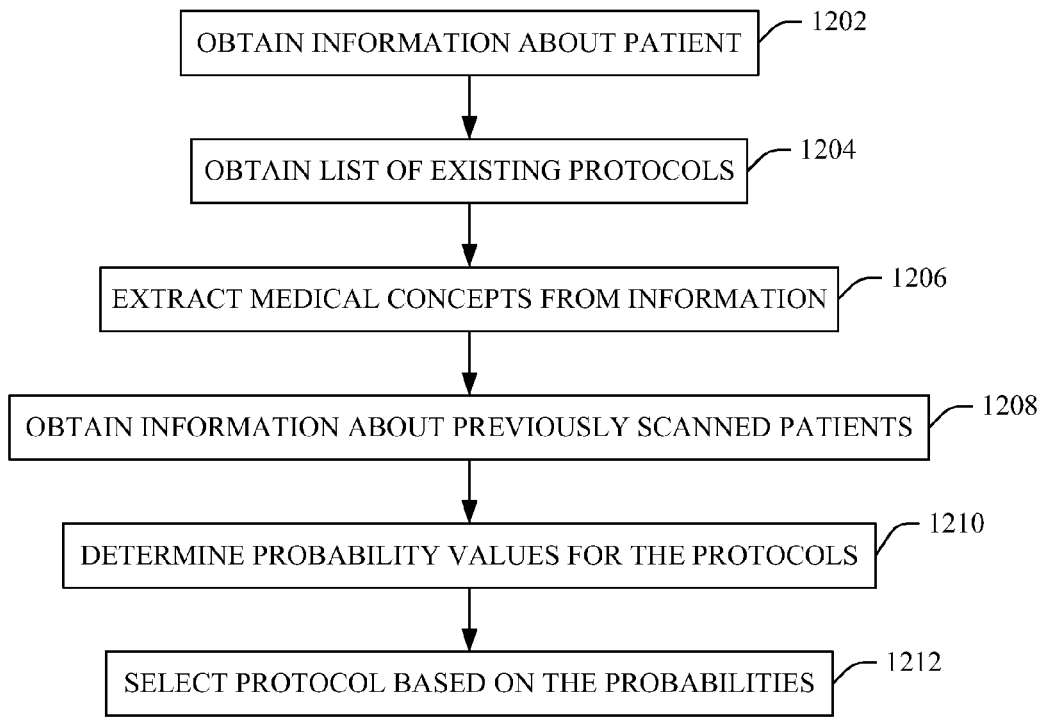
FIG. 12 illustrates an example method for recommending an imaging protocol for a patient to be scanned based on probabilities of the appropriateness of protocols for the patient.

FIG. 12 illustrates an example method for recommending an imaging protocol for a patient to be scanned based on probabilities of the appropriateness of protocols for the patient.

At 1202, information, in electronic format, about a patient to be scanned is obtained. Such information at least includes clinical indications for the patient.

At 1204, a list, in electronic format, of existing imaging protocols is obtained.

At 1206, medical concepts are extracted from the information about the patient to be scanned.

At 1208, information, in electronic format, about previous patients is obtained. Such information includes at least extracted clinical indications and previous protocols used for scanning the previous patients.

At 1210, probability values for each protocol given the medical concepts found in the extracted information for the patient to be scanned are determined. The probability values determine a likelihood of a probability for the patient.

At 1212, a protocol is selected for the patient based on the probabilities.

Figure 13:
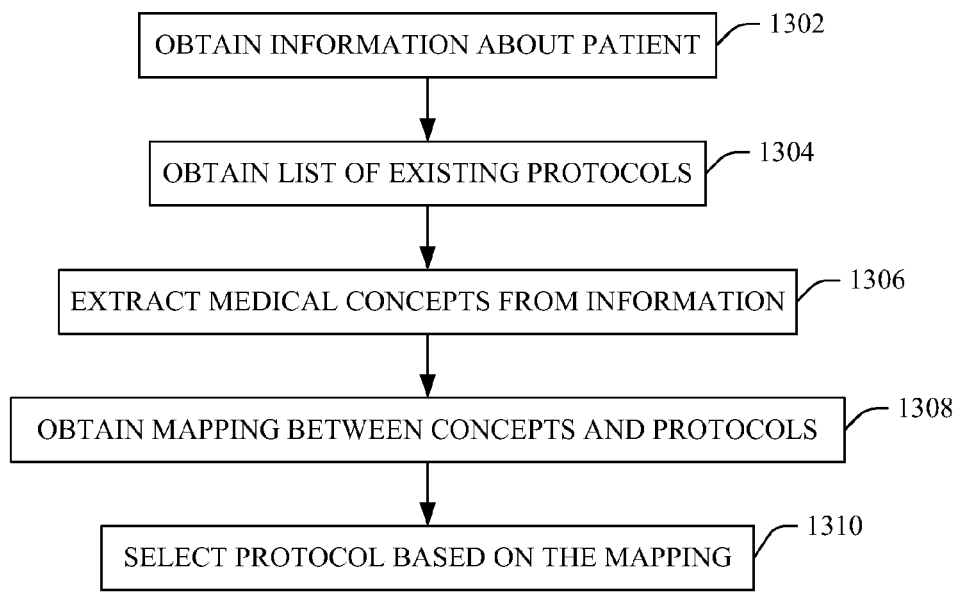
FIG. 13 illustrates an example method for recommending an imaging protocol for a patient to be scanned based on a set of pre-determined rules.

FIG. 13 illustrates an example method for recommending an imaging protocol for a patient to be scanned based on a set of pre-determined rules.

At 1302, information, in electronic format, about a patient to be scanned is obtained. Such information at least includes clinical indications for the patient.

At 1304, a list, in electronic format, of existing imaging protocols is obtained.

At 1306, medical concepts are extracted from the information about the patient to be scanned.

At 1308, a mapping between medical concepts and corresponding protocols is obtained.

At 1310, a protocol is selected for the patient based on the mapping.

The above may be implemented by way of computer readable instructions, which when executed by a computer processor(s), cause the processor(s) to carry out the described acts.

It is to be understood that the one or more processors 104 may execute and the storage medium 106 may store individually the various software applications, software modules and data for updating protocols as discussed in connection with FIGS. 1-5 or the various software applications, software modules and data for recommending protocols discussed in connection with FIGS. 6-13, a combination thereof, and/or other information.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A method, comprising:
obtaining electronically formatted information using one or more processors that includes initially selected medical imaging protocols, types of imaging procedures, sets of imaging parameters, and clinical indications from previously performed imaging procedures;
classifying the obtained electronically formatted information into groups of medical imaging protocols using one or more processors based on the initially selected medical imaging protocols;
identifying deviations between the grouped classified information and the obtained information;
generating a signal indicative of the deviations which includes a difference between at least one of: at least one of the imaging parameters in the set of imaging parameters, a type of imaging procedure, or at least one of the clinical indications; and
determining at least one recommendation based on the signal indicative of the deviations and the at least one recommendation includes at least one of: a misuse of the initially selected medical imaging protocol, an update to the initially selected medical imaging protocol; a split of the initially selected medical imaging protocol into a plurality of medical imaging protocols, or a new initially selected medical imaging protocol.

2. The method of claim 1, wherein the update to the initially selected medical imaging protocol includes at least one of:

a change in at least one of the imaging parameters of the set of imaging parameters to the initially selected medical imaging protocol;

a different modality for the initially selected medical imaging protocol; or a change in at least one of clinical indication for the initially selected medical imaging protocol.

3. The method of claim 2, wherein identifying deviations includes using an ontology to group medically related clinical indications.

4. The method of claim 3, further comprising: updating the initially selected medical imaging protocol with the recommended update which updates for at least on scanner available medical imaging protocols;

selecting the updated initially selected medical imaging protocol for imaging a patient and scanning the patient using the at least one scanner configured according to the updated initially selected medical imaging protocol.

5. The method of claim 4, wherein selecting the updated initially selected medical imaging protocol includes extracting medical concepts from collected patient information.

6. The method of claim 5, wherein the collected patient information includes information extracted from free text using natural language processing (NLP).

7. The method of claim 1, further comprising:

presenting the recommended update concurrently with one or more of the initially selected medical imaging protocols;

receiving an input indicative of a user acceptance or a user rejection of the recommended update;

updating an initially selected medical imaging protocol based on the recommended update in response to the input indicating user acceptance.

8. The method of claim 1, further comprising:

clustering the obtained electronically formatted information into clusters based on a similarity of imaging parameters; and generating at least one candidate protocol based on data indicative of at least one cluster with imaging parameters different from imaging parameters corresponding to the initially selected imaging protocol, wherein the at least one candidate protocol is utilized to create a new imaging protocol.

9. A system, comprising:

storage medium that stores computer readable instructions for at least one of updating an existing imaging protocol or creating a new imaging protocol; and one or more processors, which execute the computer readable instructions, wherein the stored computer readable instructions, when executed by the one or more processors, cause the one or more processor to obtain clinical indications for previously performed medical imaging procedures, types of the previously performed imaging procedures, and parameters used for the previously performed imaging procedures, and generate at least one of an update recommendation for a protocol corresponding to one of the previously performed medical imaging procedures, or a candidate new medical imaging protocol;

wherein the one or more processors generate the update recommendation for the protocol based on statistics about deviations between the obtained information for the previously performed medical imaging procedures and existing medical imaging protocols corresponding to the previously performed medical imaging procedures, and the deviations include at least one of a difference between at least one of: at least one of the imaging parameters in the set of imaging parameters, a type of imaging procedure, or at least one of the clinical indications.

10. The system of claim 9, wherein the one or more processors employ one or more rules to generate the update recommendation.

11. The system of claim 9, further including a display, wherein the one or more processors concurrently present the update recommendation and the medical imaging protocol corresponding to the one of the previously performed medical imaging procedure, and the update recommendation includes at least one of:

a change in at least one of the imaging parameters corresponding to the previously performed medical imaging procedure;

at least one different clinical indication for the medical imaging protocol: or a change in modality for the medical imaging protocol.

12. The system of claim 11, further including visually highlighting the update recommendation relative to the medical imaging protocol corresponding to the one of the previously performed medical imaging procedures.

13. The system of claim 11, where the one or more processors update the medical imaging protocol corresponding to the one of the previously performed medical imaging procedures with the update recommendation in response to receiving an input indicative of an acceptance of the update recommendation.

* * * * *